United States Patent
Crabtree et al.

(10) Patent No.: US 6,982,357 B2
(45) Date of Patent: Jan. 3, 2006

(54) PROCESS FOR THE PREPARATION OF PROPANE-1,3-DIOL BY VAPOR PHASE HYDROGENATION OF 3-HYDROXYPROPANAL, BETA-PROPIOLACTONE, OLIGOMERS OF BETA-PROPIOLACTONE, ESTERS OF 3-HYDROXYPROPANOIC ACID OR MIXTURES THEREOF

(75) Inventors: Simon Peter Crabtree, Durham (GB); Richard Kevin Henderson, Darlington (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/221,839

(22) PCT Filed: Mar. 14, 2001

(86) PCT No.: PCT/GB01/01128

§ 371 (c)(1),
(2), (4) Date: Jan. 30, 2003

(87) PCT Pub. No.: WO01/70659

PCT Pub. Date: Sep. 27, 2001

(65) Prior Publication Data

US 2003/0153795 A1   Aug. 14, 2003

(30) Foreign Application Priority Data

Mar. 20, 2000  (GB) .......................................... 0006722
Aug. 22, 2000  (GB) .......................................... 0020738

(51) Int. Cl.
    C07C 29/136  (2006.01)
    C07C 29/14   (2006.01)
    C07C 29/141  (2006.01)
    C07C 29/147  (2006.01)
    C07C 29/149  (2006.01)

(52) U.S. Cl. .................... 568/864; 568/852; 568/861; 568/862; 568/863

(58) Field of Classification Search ................ 568/864, 568/861, 862, 863, 852
See application file for complete search history.

(56) References Cited

U.S. PATENT DOCUMENTS 2,782,226 A    2/1957   Seon et al.
3,260,738 A    7/1966   McClure et al.
3,770,837 A    11/1973  Favstritsky et al.
4,094,914 A    6/1978   Rottig et al.
4,209,467 A    6/1980   Kojima et al.
4,511,744 A    4/1985   Miyazaki et al.
4,634,780 A    1/1987   Alper et al. ................ 549/273
4,665,213 A    5/1987   Alper et al.
4,762,817 A    8/1988   Logsdon et al.
4,855,515 A    8/1989   Morris et al.
4,876,402 A    10/1989  Logsdon et al.
4,945,179 A    7/1990   Drent ......................... 560/233
5,030,609 A    7/1991   Turner et al.
5,171,898 A    12/1992  Arntz et al.
5,281,752 A    1/1994   Fujiwara et al. ............ 562/522
5,310,948 A    5/1994   Drent et al. ................ 549/328
5,334,778 A    8/1994   Haas et al. ................. 568/862
5,359,081 A    10/1994  Drent et al. ................ 549/328
5,364,987 A    11/1994  Haas et al. ................. 568/866
5,527,973 A    6/1996   Kelsey ....................... 568/682
5,585,528 A    12/1996  Powell et al. ............... 568/862
5,770,776 A    6/1998   Powell et al. ............... 568/862
5,786,524 A    7/1998   Powell et al. ............... 568/682
5,821,092 A    10/1998  Nagarajan et al. .......... 435/158
5,981,808 A    11/1999  Powell et al. ............... 568/862
6,191,321 B1   2/2001   Forschner et al.

FOREIGN PATENT DOCUMENTS

DE   37 37 277 A1      5/1988
EP   0 854 709 A1      8/1998
EP   1034842           9/2000
GB   2 199 766 A       7/1988
GB   1020575           2/1996
WO   WO 99/48852    *  9/1999
WO   WO 00/14041       3/2000

* cited by examiner

Primary Examiner—Elvis O. Price
(74) Attorney, Agent, or Firm—Davidson, Davidson & Kappel, LLC

(57) ABSTRACT

A process is described for the production of propane-1,3-diol. The process comprises subjecting a vaporous feed mixture comprising a hydrogen-containing gas and a feedstock selected from 3-hydroxypropanal, β-propiolactone, oligomers of β-propiolactone, esters of 3-hydroxypropanoic acid, and mixtures of two or more thereof to hydrogenation conditions in a hydrogenation zone in the presence of a heterogeneous hydrogenation catalyst, and recovering a reaction product comprising propane-1,3-diol.

7 Claims, No Drawings

PROCESS FOR THE PREPARATION OF PROPANE-1,3-DIOL BY VAPOR PHASE HYDROGENATION OF 3-HYDROXYPROPANAL, BETA-PROPIOLACTONE, OLIGOMERS OF BETA-PROPIOLACTONE, ESTERS OF 3-HYDROXYPROPANOIC ACID OR MIXTURES THEREOF

This invention relates to the production of propane-1,3-diol.

Propane-1,3-diol is used as an intermediate in the production of polyesters for production of fibres or films. It can be prepared by a two-step process in which ethylene oxide is subjected to an oxonation reaction followed by hydrogenation:

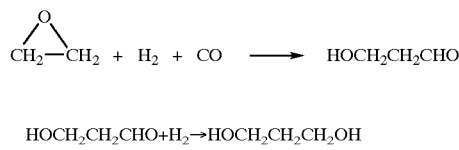

$$HOCH_2CH_2CHO + H_2 \rightarrow HOCH_2CH_2CH_2OH$$

U.S. Pat. No. 5,981,808 describes the use of a non-phosphine-ligated cobalt compound as oxonation catalyst in an essentially non-water-miscible solvent followed by water extraction to separate the catalyst from the 3-hydroxypropanal produced as oxonation product. The aqueous mixture containing the 3-hydroxypropanal is then subjected to hydrogenation. U.S. Pat. No. 5,585,528 proposes addition of a lipophilic tertiary amine as a promoter in such a process. Use of methyl t-butyl ether for extraction of the aqueous mixture to recover cobalt catalyst for re-use is described in U.S. Pat. No. 5,770,776. U.S. Pat. No. 5,786,524 teaches a similar process and proposes the use of a rhodium catalyst as an alternative catalyst in the oxonation step.

It is, however, a drawback of such a process that high levels of byproducts are produced during liquid phase hydrogenation of the intermediate 3-hydroxypropanal under the recommended hydrogenation conditions, namely liquid phase hydrogenation at 220° C. and 100 bar (1000 kPa). Under such conditions the conversion of 3-hydroxypropanal is only about 90% while up to 10% is converted to byproducts.

It has also been proposed to combine the oxonation and hydrogenation steps into a one-step process with, it is claimed, minimal production of 3-hydroxypropanal as byproduct. Such a one-step process can be effected using a phosphine complex of cobalt carbonyl as the major catalyst ingredient. However, the use of a ruthenium compound as catalyst has also been proposed. An organic solvent is used in the reaction enabling a water extraction to be used in order to separate propane-1,3-diol from the oxonation mixture. Ethylene oxide conversions of 55% with a selectivity towards propane-1,3-diol of 87% are reported.

U.S. Pat. Nos. 5,310,948 and 5,359,081 teach formation of β-propiolactone or polymers thereof by reaction of carbon monoxide and ethylene oxide in the presence of a cobalt-containing catalyst system comprising a source of cobalt and a hydroxyl-substituted pyridine.

Propane-1,3-diol can alternatively be produced from glycerol using recombinant bacteria expressing recombinant diol dehydratase. Such a process is taught in U.S. Pat. No. 5,821,092.

It has also been proposed to subject acrolein to hydration so as to form 3-hydroxypropanal which is then hydrogenated. In this connection reference may be made to U.S. Pat. No. 5,364,987.

In U.S. Pat. No. 5,334,778 it is proposed to produce propan-1,3-diol having a residual carbonyl content below 500 ppm by catalytically hydrogenating 3-hydroxypropanal in aqueous solution in the presence of a hydrogenation catalyst at 30° C. to 80° C. to a 3-hydroxypropanal conversion of 50% to 95% and then continuing the hydrogenation at 120° C. to 140° C. to achieve a 3-hydroxypropanal conversion of substantially 100%.

Both glycerol and acrolein are, however, generally more expensive and less available than ethylene oxide. Hence it is not currently an economic proposition to manufacture propane-1,3-diol by either of these last two mentioned processes.

It would be desirable to provide an improved process for the production of propane-1,3-diol. It would further be desirable to provide a process for producing propane-1,3-diol by hydrogenation of an appropriate carbonyl compound which exhibits increased selectivity towards propane-1,3-diol and reduced amounts of undesirable byproducts, such as propan-1-ol, which cannot readily be converted to propane-1,3-diol. It would further be desirable to provide a process for the production of propane-1,3-diol by hydrogenation of an intermediate compound which can be made from ethylene oxide and which contains at least one carbon-oxygen double bond, such as β-propiolactone, oligomers of β-propiolactone, or an ester of 3-hydroxypropionic acid, with minimal formation of undesirable byproducts.

It is accordingly an objective of the present invention to provide an improved process for the production of propane-1,3-diol. In addition the present invention seeks to provide a hydrogenation process for producing propane-1,3-diol that uses in a hydrogenation step an optimised catalyst system. Yet a further objective of the present invention is to provide a process for the production of propane-1,3-diol by hydrogenation of an intermediate compound which can be made from ethylene oxide, such intermediate compound containing at least one carbon-oxygen double bond, and preferably being selected from, β-propiolactone, oligomers of β-propiolactone, esters of 3-hydroxypropionic acid, and mixtures of two or more thereof, with reduced amounts being formed of undesirable byproducts, such as propan-1-ol, which cannot readily be converted to the desired propane-1,3-diol.

According to the present invention there is provided process for the production of propane-1,3-diol which comprises forming a vaporous feed mixture comprising a hydrogen-containing gas and a substantially anhydrous feedstock selected from β-propiolactone, oligomers of β-propiolactone, esters of 3-hydroxypropanoic acid, and mixtures of two or more thereof, supplying the vaporous feed mixture to a hydrogenation zone containing a heterogeneous hydrogenation catalyst selected from reduced copper oxide/zinc oxide hydrogenation catalysts, reduced manganese-promoted copper catalysts, reduced copper chromite catalysts and reduced promoted copper chromite catalysts at a temperature of from about 130° C. to about 180° C. and a feed pressure to the hydrogenation zone of from about 50 psia (about 344.74 kpa) to about 2000 psia (13789.52 kPa) said hydrogenation conditions effective for hydrogenating feedstock to propane-1,3-diol, and recovering from the hydrogenation zone a reaction product comprising propane-1,3-diol.

The feedstock to the hydrogenation step is substantially anhydrous, that is to say it contains no more than about 5% (w/v), preferably no more than about 1% (w/v), and even more preferably less than about 0.1% (w/v) of water. It is selected from β-propiolactone, oligomers of β-propiolactone, and esters of 3-hydroxypropanoic acid, and mixtures of two or more thereof. β-propiolactone can self-polymerise to form oligomers of β-propiolactone. The presence of more than a minor amount of such oligomers in the feedstock to the hydrogenation zone is generally undesirable because of their relative lack of volatility. Hence it will normally be preferred to use a feedstock to the hydrogenation zone which contains less than about 10 molar % of oligomers of β-propiolactone. Accordingly it will usually be preferred to minimise the proportion of oligomers of β-propiolactone in the feedstock to the hydrogenation zone.

Hydrogenation is effected using a vaporous feed mixture to the hydrogenation zone, this mixture containing in addition to the feedstock also a hydrogen-containing gas. The hydrogen-containing gas is preferably substantially free from carbon oxides but may contain one or more inert gases, such as nitrogen, argon and helium, in amounts of up to 50% v/v, but which preferably do not exceed about 10% v/v and more preferably do not exceed about 5% v/v, e.g. about 1% v/v or less.

The hydrogenation conditions may be selected so that the reaction mixture exiting the hydrogenation zone is also in the vapour phase. However, it is alternatively possible, and indeed may be preferable, to utilise hydrogenation conditions such that the reaction mixture at the exit end of the hydrogenation zone is below its dew point so that at least some of the condensable components thereof are present in the liquid phase.

The hydrogenation zone conveniently contains a fixed bed of a granular hydrogenation catalyst. If desired, the hydrogenation zone can contain more than one catalyst bed and the hydrogenation catalyst of one bed can, if desired, differ from the hydrogenation catalyst of at least one other bed.

The active catalytic species in the hydrogenation catalyst may be at least partially supported on a supporting material selected from chromia, zinc oxide, alumina, silica, silica-alumina, silicon carbide, zirconia, titania, carbon, or a mixture of two or more thereof, for example, a mixture of chromia and carbon.

Preferably the hydrogenation catalyst is a reduced manganese-promoted copper catalyst. Such manganese-promoted copper catalysts preferably have a total surface area of at least about 15 m$^2$/g, more preferably at least about 20 m$^2$/g, and even more preferably at least about 25 m$^2$/g, in the unreduced form.

A particularly preferred hydrogenation catalyst is a reduced manganese-promoted copper catalyst which is available as DRD92/89A catalyst from Kvaerner Process Technology Limited of The Technology Centre, Princeton Drive, Thornaby, Stockton-on-Tees, TS17 6PY, England. Alternatively there may be used a reduced manganese-promoted copper catalyst which is available as DRD92/89B catalyst from Kvaerner Process Technology Limited.

The hydrogenation step is conducted under vapour phase feed conditions so that the feed stream to the hydrogenation zone is above its dew point and is thus a vaporous feed stream. The reaction product mixture from the hydrogenation zone can also be recovered at a temperature above its dew point so that it too is in vaporous form or it can be recovered at a temperature below its dew point so that at least part of the condensable components thereof are in liquid form.

Although it is possible to conduct the hydrogenation process of the present invention in a tubular reactor under substantially isothermal conditions, it will normally be preferred to operate under substantially adiabatic hydrogenation conditions using a fixed catalyst bed or beds since adiabatic reactors are much cheaper to construct than tubular reactors. However, care should be taken in designing the plant, in particular in selecting a suitable gas:feedstock ratio and in choosing a catalyst size, that the temperature rise across any catalyst bed is limited to a reasonable value, typically not more than about 20° C., so as to keep the temperature to which the reaction mixture is exposed within desired limits. In this way the formation of 1-propanol as a byproduct can be limited.

It will normally be preferred that, in the vaporous feed stream to the hydrogenation zone, the hydrogen-containing gas:feedstock molar ratio shall be in the range of from about 50:1 to about 1000:1.

Typically the feed temperature to the hydrogenation zone is from about 130° C. to about 180° C., more preferably from about 135° C. to about 150° C., while the feed pressure to the hydrogenation zone is from about 50 psia (about 344.74 kPa) to about 2000 psia (about 13789.52 kPa), for example, from about 350 psia (about 2413.17 kPa) to about 1000 psia (about 6894.76 kPa). The feedstock is also preferably supplied to the first hydrogenation zone at a rate corresponding to a liquid hourly space velocity of from about 0.05 to about 5.0 h$^{-1}$. Preferably unreacted hydrogen-containing gas is recycled for further use.

If desired, the feedstock to the hydrogenation zone can be diluted with a solvent, such as methanol, which is stable under the hydrogenation conditions utilised.

The invention is further illustrated in the following Examples.

EXAMPLE 1

This Example was intended to provide a simulation of conditions similar to those that might exist in a commercial hydrogenation reactor for hydrogenation of methyl 3-hydroxypropionate utilising recycled hydrogen which would be saturated with methanol co-product.

A solution of crude methyl 3-hydroxypropionate (approximately 90% pure) was diluted with an approximately equal weight of methanol to form a feed solution. This feed solution was subjected to vapour phase hydrogenation in a once-through adiabatic fixed-bed reactor. The reactor was constructed from a 95 cm length of 20.96 mm internal diameter tube which was oil-jacketed to reduce heat losses. The reactor contained a charge of 100 ml of DRD92/89A catalyst which is obtainable from Kvaerner Process Technology Limited of The Technology Centre, Princeton Drive, Thornaby, Stockton-on-Tees, TS17 6PY, England. The catalyst was reduced by a procedure analogous to that described in U.S. Pat. No. 5,030,609.

The feed solution was supplied at a feed rate of 12 ml/h to a heater and vaporised by a stream of pure hydrogen at a rate of 1000 Nl/h (i.e. 1000 liters per hour measured at 760 mm Hg [101.33 kPa] and 0° C.). The vaporous mixture was passed over the catalyst at a pressure of 400 psig (2757.90 kPa gauge) and a temperature of 138° C. The reaction product mixture exiting the reactor was cooled and the condensed liquid collected. The feed and product were analysed by gas chromatography using a 60 meter CP SIL 19 capillary column of 0.32 mm internal diameter with a 1.3 μm film thickness.

Conversion of the methyl 3-hydroxypropionate was determined as 73.3% with a selectivity to propane-1,3-diol of 83.4% and to 1-propanol of 5.8%. It is believed that the byproducts comprise mainly materials which, upon hydrogenation, can be converted to propane-1,3-diol and hence can be recycled.

EXAMPLE 2

The general procedure of Example 1 was repeated except that the temperature was 148° C. Conversion of the methyl 3-hydroxypropionate was determined as 84.9% with a selectivity to propane-1,3-diol of 84.8% and to 1-propanol of 7.2%. Operation at this slightly higher temperature provides an expected increase in conversion with a minor increase in selectivity to 1-propanol.

EXAMPLE 3

The general procedure of Example 1 was repeated except that the temperature was 174° C. Conversion of the methyl 3-hydroxypropionate was determined as 99.95% with a selectivity to propane-1,3-diol of 13.1% and to 1-propanol of 81.8%. This shows that operation at high temperature favours formation of the alcohol, 1-propanol, rather than propan-1,3-diol.

EXAMPLE 4

The same feed solution as used in Example 1 was subjected to vapour phase hydrogenation in an adiabatic fixed-bed reactor system which incorporated recycle of excess gas following condensation of the reactor product stream. Make-up pure hydrogen was supplied to the system to maintain constant system pressure. The reactor was constructed from a 200 cm length of 26.64 mm internal diameter tube which was insulated and provided with electric trace heating means to prevent net heat loss from the reactor. The reactor contained a charge of 250 ml of DRD92/89A catalyst. The catalyst was reduced by a procedure analogous to that described in U.S. Pat. No. 5,030,609.

The feed solution was fed at a rate of 80 ml/h to a heater and vaporised by a stream of mixed recycle gas and pure hydrogen at a rate of 10900 Nl/h. The vaporous mixture was passed over the catalyst at a pressure of 885 psig (6101.86 kPa gauge) and an inlet temperature of 149° C. The outlet temperature was measured as 150° C. The reactor product mixture was cooled and the condensed liquid collected. The feed and product were analysed by gas chromatography using a 60 meter CP SIL 19 capillary column of 0.32 mm internal diameter with a 1.3 μm film thickness.

Conversion of the methyl 3-hydroxypropionate was determined as 77.8% with a selectivity to propane-1,3-diol of 78.9% and to 1-propanol of 14.8%.

EXAMPLE 5

The general procedure of Example 4 was repeated except that the inlet pressure was 735 psig (5067.65 kPa), and the mixed recycle and pure hydrogen make-up flow rate was 8116 Nl/h. Conversion of the methyl 3-hydroxypropionate was determined as 61.1% with a selectivity to propane-1,3-diol of 79.0% and to 1-propanol of 14.4%. Operation at this lower pressure and lower gas rate provides an expected reduced conversion but with similar selectivities to propane-1,3-diol and to 1-propanol.

EXAMPLE 6

A solution of crude methyl 3-hydroxypropionate (approximately 98% pure) was diluted with an approximately equal weight of methanol to form a feed solution. This feed solution was subjected to vapour phase hydrogenation in the apparatus used in Example 4.

The feed solution was fed at a rate of 80.8 ml/h to a heater and vaporised by a stream of mixed recycle gas and pure hydrogen at a rate of 8717 Nl/h. The vaporous mixture was passed over the catalyst at a pressure of 885 psig (6101.86 kPa gauge) and an inlet temperature of 148° C. The outlet temperature was measured as 149° C.

The reactor product mixture was cooled and the condensed liquid collected.

The feed and product were analysed by the method used in Example 4.

Conversion of the methyl 3-hydroxypropionate was determined as 71.3% with a selectivity to propane-1,3-diol of 80.6% and to 1-propanol of 12.5%. It is believed that the byproducts comprise mainly materials which, upon hydrogenation, can be converted to propane-1,3-diol and hence can be recycled.

EXAMPLE 7

The general procedure of Example 6 was repeated except that the feed rate was 61.4 ml/h, the recycle stream was 6537 Nl/h and the inlet temperature was 149° C. The outlet temperature was measured as 150° C.

Conversion of the methyl 3-hydroxypropionate was determined as 84.1% with a selectivity to propane-1,3-diol of 73.7% and to 1-propanol of 21.5%.

EXAMPLE 8

The general procedure of Example 7 was repeated except that the inlet temperature was 154° C. The outlet temperature was measured as 155° C.

Conversion of the methyl 3-hydroxypropionate was determined as 87.3% with a selectivity to propane-1,3-diol of 75.2% and to 1-propanol of 18.7%.

EXAMPLE 9

The general procedure of Example 8 was repeated except that the mixed recycle and pure hydrogen make-up flow rate was 5226 Nl/h and the inlet temperature was 152° C. The outlet temperature was measured as 153° C.

Conversion of the methyl 3-hydroxypropionate was determined as 86.7% with a selectivity to propane-1,3-diol of 76.2% and to 1-propanol of 16.9%.

What is claimed is:

1. A process for the production of propane-1,3-diol which comprises
    forming a vaporous feed mixture comprising a hydrogen-containing gas and a substantially anhydrous feedstock selected from β-propiolactone, oligomers of β-propiolactone, esters of 3-hydroxypropanoic acid, and mixtures of two or more thereof,
    supplying the vaporous feed mixture to a hydrogenation zone containing a heterogeneous hydrogenation catalyst selected from reduced copper oxide/zinc oxide hydrogenation catalysts, reduced manganese-promoted copper catalysts, reduced copper chromite catalysts and reduced promoted copper chromite catalysts at a temperature of from about 130° C. to about 180° C. and a feed pressure to the hydrogenation zone of from about 50 psia (about 344.74 kpa) to about 2000 psia (13789.52 kPa) said hydrogenation conditions effective for hydrogenating feedstock to propane-1,3-diol, and
    recovering from the hydrogenation zone a reaction product comprising propane-1,3-diol.

2. The process according to claim 1, wherein the feedstock comprises an alkyl ester or a hydroxyalkyl ester of 3-hydroxypropanoic acid.

3. The process according to claim 1 wherein the hydrogenation is effected using a fixed bed of a granular hydrogenation catalyst.

4. The process according to claim 1 wherein the hydrogen-containing gas:feedstock molar ratio in the vaporous feed mixture is in the range of from about 50:1 to about 1000:1.

5. The process according to claim 1, wherein the feed temperature to the hydrogenation zone is from about 135° C. to about 150 ° C.

6. The process according to claim 1 wherein the feed pressure to the hydrogenation zone is from about 350 psia (about 2413.17) to about 1000 psia (about 6894.76 kPa).

7. The process according to claim 1 wherein the feedstock is supplied to the first hydrogenation zone at a rate corresponding to a liquid hourly space velocity of from about 0.05 to about 5.0 $h^{-1}$.

* * * * *